United States Patent

Sommer

(10) Patent No.: US 7,813,838 B2
(45) Date of Patent: Oct. 12, 2010

(54) MEDICAL EXAMINATION AND TREATMENT APPARATUS

(75) Inventor: Andres Sommer, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 1012 days.

(21) Appl. No.: 11/214,679

(22) Filed: Aug. 29, 2005

(65) Prior Publication Data

US 2006/0058919 A1    Mar. 16, 2006

(30) Foreign Application Priority Data

Aug. 31, 2004   (DE)   ................. 10 2004 042 489

(51) Int. Cl.
G05B 19/18    (2006.01)
B25J 19/00    (2006.01)

(52) U.S. Cl. ............... 700/254; 700/250; 318/568.12; 318/568.24; 901/1.2; 901/49

(58) Field of Classification Search ......... 700/245, 700/246, 250, 254, 260, 261, 262; 318/568.12, 318/568.24; 901/1.2, 49; 702/188
See application file for complete search history.

(56) References Cited

U.S. PATENT DOCUMENTS

| | | | |
|---|---|---|---|
| 5,142,930 A | | 9/1992 | Allen et al. |
| 5,351,925 A | | 10/1994 | Druais |
| 5,408,409 A | | 4/1995 | Glassman et al. |
| 5,704,791 A | * | 1/1998 | Gillio ........................ 434/262 |
| 5,755,577 A | * | 5/1998 | Gillio ........................ 434/262 |
| 5,790,307 A | | 8/1998 | Mick et al. |
| 5,791,908 A | * | 8/1998 | Gillio ........................ 434/262 |
| 5,800,177 A | * | 9/1998 | Gillio ........................ 434/262 |
| 5,800,178 A | * | 9/1998 | Gillio ........................ 434/262 |
| 5,882,206 A | * | 3/1999 | Gillio ........................ 434/262 |
| 5,964,647 A | | 10/1999 | Henky |
| 6,470,205 B2 | * | 10/2002 | Bosselmann et al. ........ 600/424 |
| 6,828,788 B2 | * | 12/2004 | Wang ........................ 324/309 |
| 2004/0077939 A1 | | 4/2004 | Graumann |
| 2004/0106916 A1 | | 6/2004 | Quaid et al. |

(Continued)

FOREIGN PATENT DOCUMENTS

DE    42 19 939 C2    12/1993

(Continued)

OTHER PUBLICATIONS

Mack, Minimally Invasive and Robotic Surgery, 2001, Internet, p. 568-572.*

(Continued)

*Primary Examiner*—Khoi Tran
*Assistant Examiner*—Brian J Broadhead
(74) *Attorney, Agent, or Firm*—Brinks, Hofer, Gilson & Lione

(57) ABSTRACT

A medical examination and treatment apparatus includes a robot operable to control a tool, and an internal position-determination system to measure a position of the tool by determining a setting of adjusting elements of the robot. The apparatus further includes an external position-determination system to measure the position of the tool, and a position monitoring system to compare the position of the tool determined by the internal position-determination system with the position of the tool determined by the external position-determination system. A mobility of the tool is restricted if an adjustable threshold relating to deviations between position measurements is exceeded.

23 Claims, 1 Drawing Sheet

U.S. PATENT DOCUMENTS

2004/0111183 A1 6/2004 Sutherland et al.
2004/0116172 A1 6/2004 Hall

FOREIGN PATENT DOCUMENTS

| DE | 44 12 605 A1 | 10/1995 |
| DE | 101 08 547 A1 | 10/2002 |
| DE | 20 2004 003 301 U1 | 7/2004 |
| EP | 0 220 501 B1 | 5/1989 |
| EP | 0 456 102 A2 | 5/1991 |
| EP | 1 479 964 A2 | 5/2004 |
| WO | WO 97/40766 A1 | 11/1997 |
| WO | WO 97/46923 A1 | 12/1997 |
| WO | WO 2004/014244 A2 | 2/2004 |
| WO | WO 2004/052225 A2 | 6/2004 |

OTHER PUBLICATIONS

German Office Action for DE 10 2004 042 489.6-35 dated Jan. 16, 2007 and English translation.

* cited by examiner

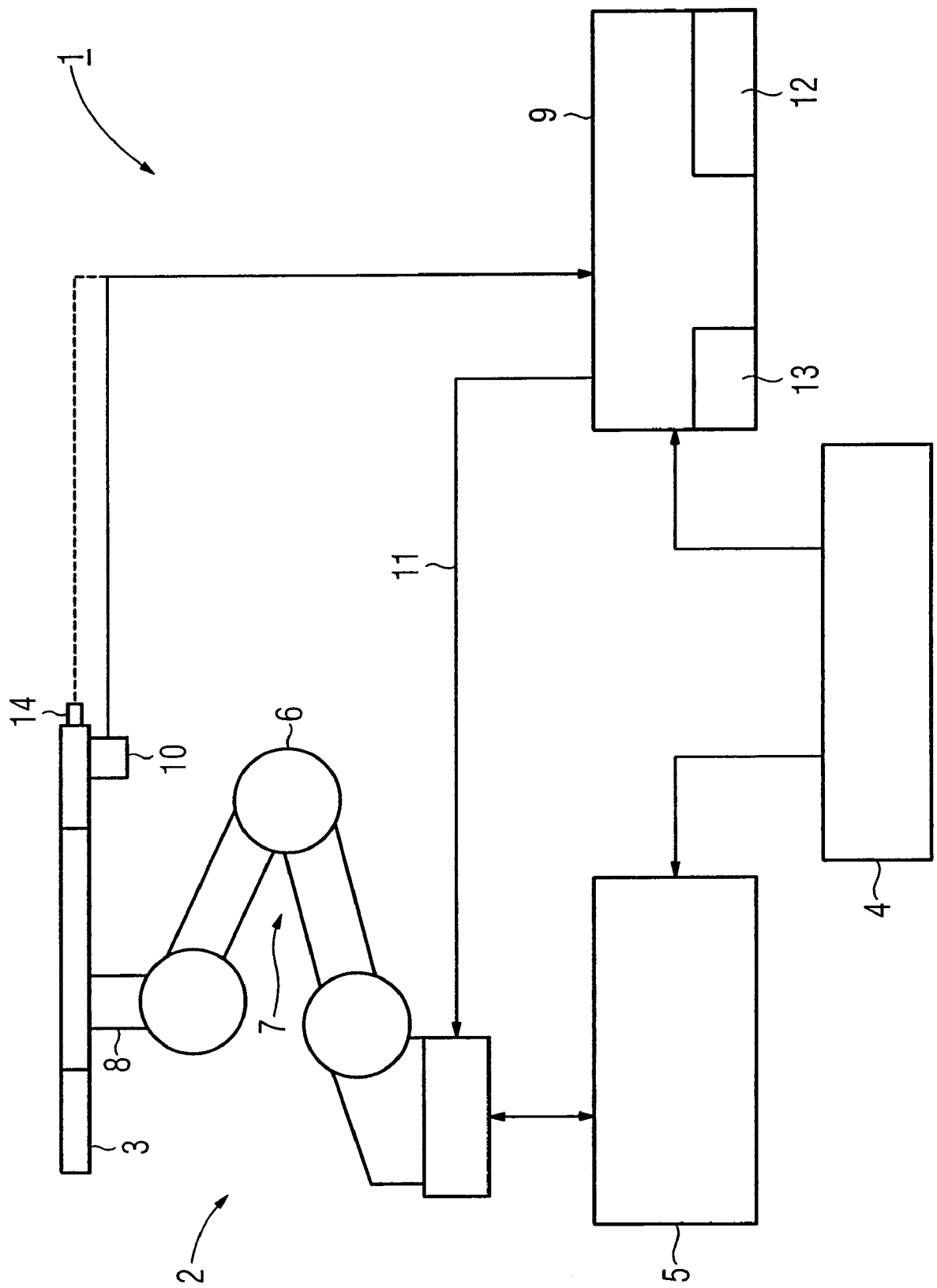

MEDICAL EXAMINATION AND TREATMENT APPARATUS

FIELD

The present embodiments relate, in general, to medical examination and/or treatment systems, and in particular, to a method for operating a medical examination and/or treatment apparatus.

BACKGROUND

From German Patent Disclosure DE 101 08 547 A1, an apparatus and a method for controlling surgical instruments in a surgical operation is known. The surgical instrument is guided by a robot or manipulator. The area of a patient, such as a knee, in which a surgical operation is performed with the surgical instrument is imaged during the operation by an X-ray system. In the X-ray image, a view of the surgical instrument is incorporated in a correct position. A position-detecting device detects both the position of the X-ray system and the position of the robot. The position of the area of the patient in which the operation is performed is also detected. In order to establish a relationship between the spatial position of the surgical instrument and the spatial position of the area in which the operation is to be performed, the relation between the working area, such as the tip, of the surgical instrument and the positioning of the robot is known. The position of the working area of the surgical instrument is thus not detected directly.

From EP 0 220 501 B1, an X-ray diagnostic system with system components that are adjustable by a control device is known. An X-ray tube, a picture-taking system, and a patient bed are provided as the components of the system, each individually adjustable in three dimensions. Each of the system components can be suspended from adjusting mechanisms in the manner of robot arms. As a safety device, a television camera aimed at the freely spatially movable system components may be provided, which is connected to a computer in such a way that the positions in which objects or persons recognized by the television camera are located are blocked. Moving equipment or parts may also be equipped with optical, tactile or ultrasound sensors. Such sensors on movably supported equipment or parts recognize an approach to an object or a person but do not serve as an absolute measurement system.

In US Patent Application 2004/0106916 A1, a computer-controlled guidance system and a method for surgical procedures are described. A surgical instrument is moved, with the aid of a haptic device that is triggered by commands of a surgeon, toward a target area on a patient. In a computer-assisted surgery system (CAS), virtual haptic objects are determined that guide and/or restrict movements and a working procedure of the surgical instrument.

In general, when robots are used in human surroundings, stringent safety demands need to be met. As a rule, the working area of the robot may not be accessible by the persons using or controlling the robot. Typical examples of safety devices are photoelectric beams which shut off or stop the robot as soon as a human or an object comes relatively close to the robot's working area. However, the photoelectric beam does not affect courses of motion of the robot, as long as the human or the object is permissibly located outside the working area or range of the robot. Thus, the photoelectric beam intervenes in the operation of the robot only in an extreme case, but does not contribute to improving or increasing the safety of the courses of motion of the robot during intended operations.

BRIEF SUMMARY

The present invention is defined by the appended claims. This description summarizes some aspects of the present embodiments and should not be used to limit the claims.

Potential applications of robots, such as bent robot arms, may be improved or expanded in the field of medical technology.

Hereafter, features and advantages recited in connection with an apparatus apply accordingly to a method, and vice versa. A medical examination and/or treatment apparatus includes a robot, which guides a tool that is used in a medical examination and/or treatment. The term "tool" is to be understood broadly and includes all types of objects that can be carried or manipulated by a robot or adjusted under robot actuation in any way in a medical apparatus. Moreover, a tool is also understood to be a patient bed held by a robot.

A bent robot arm is used as the robot, which is installed either in stationary form or movably, for example drivable on wheels, in the examination and/or treatment room. The robot may have a configuration that is known from robots used in manufacturing or other robots.

The robot is equipped with an internal position-determination system which is intended for measuring the position of the tool by determining a setting of adjusting elements of the robot. If the robot is configured as a bent robot arm, the adjusting elements are the joints of the robot. Instead of joints or in addition to joints, linear guides of the robot may also be provided. As such, the robot is equipped with suitable linear measurement systems. Regardless of the distinctive kinematics of the robot, the measurement systems that are internal to the robot and that form the internal position-determination system suffice to determine the position of the tool, such as that of the patient bed.

The examination and/or treatment apparatus further includes an external position-determination system which is intended for measuring the position of the tool independently of the robot. The external position-determination system may be based on different physical measurement principles than the internal position-determination system; that is, configured differently from the internal position-determination system. The external position-determination system measures the position and/or the motion of the tool directly. In contrast to the internal position-determination system, the setting of the adjustable parts of the robot does not enter into the measurement. Depending on the intended use and on the accuracy required, the external position-determination system can work with gyrostats, satellite navigation (GPS), or optical location and navigation systems, for example. A camera-supported measurement system may be used, and in an advantageous feature, pictures taken by a plurality of cameras are automatically evaluated three-dimensionally.

The internal position-determination system may be linked to the external position-determination system in a position monitoring system. The position of the tool measured by the internal position-determination system is compared continuously and automatically with the position of the tool measured by the external position-determination system. A continuous comparison of the measurement findings determined by the various position monitoring systems is understood hereafter to mean not only a continuous comparison in the strict sense but also a comparison that is repeated at short time intervals, of for example less than 1 second or less than 0.1 seconds. The second, external position-determination system, accordingly, comes into play not only when the tool of the robot departs from an intended working area, and/or an object penetrates the working range in a way that threatens safety, as is the case for example with photoelectric beam safety devices or safety systems that use proximity sensors, but is also operated permanently and synchronously with the first position-determination system that is internal to the robot.

The comparison performed continuously or at least at brief time intervals, such as of less than 1 second, between the measured values determined by the various position-determination systems leads in general to a finding of deviation values. These deviation values are compared with an adjustable threshold value. If the threshold value is exceeded, the mobility of the tool is restricted, and the tool may be stopped. The settability or setting of the threshold value has a distinguishable advantage that a sensitivity of the position monitoring system can be adapted to the corresponding requirements of the medical application. For example, in treatments such as particle radiation treatments, which demand substantially high geometric precision, the threshold value can be set low.

In one further embodiment, the value or level of the threshold is dependent on a speed of movement of the tool. The demands for positioning precision are variously high, depending on the motion status of the tool. For example, during an advancement motion, with which the tool is brought into an examination and/or treatment position, greater geometric tolerances can be expected than in an ensuing operation of the tool in the examination and/or treatment position with substantially or extremely slight advancement. As such, the threshold value may be expediently set lower, the slower the tool is moved. Different regions in space in the treatment and/or examination room can also be determined, within which the threshold value that indicates an allowable degree of deviation in the variously obtained position values of the tool is substantially variously high. The threshold value, that is, the tolerance value or level, can be set higher, as long as the tool, and when applicable the patient bed, is located outside an examination and/or treatment region, approximately in a region in which the patient is located, before he/she is shifted by the robot into the examination and/or treatment position. However, even in the region outside the actual examination and/or treatment region, the position monitoring system is sensitive enough to prevent states of motion of the tool that are critical in regard to safety.

Moreover, the examination and/or treatment apparatus may be equipped with a collision monitoring system, which is coupled to the position monitoring system and likewise brings about substantially fast stopping of the tool as needed, that is, if a potential collision is detected. In an advantageous feature, an acceleration measurement system that detects accelerations, and sudden loads, of the tool may be coupled with the position monitoring system and likewise serves to detect impermissible operating states and optionally stops the tool or returns it in a determined way.

By coupling a first position-determination system internal to the robot with a second position-determination system independent of the robot, the usage possibilities of a robot in medical applications may be expanded considerably; the degree of error tolerance can be adapted to the applicable demands determined by the medical examination or treatment methods.

One illustrative and exemplary embodiment of the invention is described in further detail below with reference to, and in conjunction with, the FIGURE.

BRIEF DESCRIPTION OF A VIEW OF THE DRAWING

FIG. 1 schematically shows an exemplary embodiment of a medical examination and/or treatment apparatus.

DETAILED DESCRIPTION

A schematically represented examination and/or treatment apparatus 1 has a robot 2, namely a bent robot arm, which carries or supports a patient bed as the tool 3. The components of the examination and/or treatment apparatus 1 intended for performing the medical examination or treatment, such as an X-ray system or a particle radiation system, are not shown in the drawing. The patient (not shown), resting on the patient bed 3 and immobilized if needed, is brought into the examination and/or treatment position by the robot 2. During the examination or treatment, the components, not shown, of the examination and/or treatment apparatus 1 are adjusted. Moreover, the patient bed 3 may also be moved in a predetermined way during the examination and/or treatment.

The targeted position of the patient bed 3 is determined by a control unit 4 and is sent to a control system 5 of the robot 2. The robot 2 adjusts the patient bed 3 to suit the determined and targeted position, with multiple joints 6 of the robot 2 being used as the adjusting elements. In a manner not shown, the robot 2, or parts of the robot 2, may also be moved linearly, as triggered by the control system 5. In each case, the setting of the adjusting elements 6 can be measured by an internal position-determination system 7 of the robot 2, which is not visible in detail but cooperates with the control system 5, so that given the prerequisite of a known geometrical relationship between the robot arm 8 that carries the tool 3 and the tool 3 itself, the positioning of the tool 3 can be determined unequivocally.

From the control unit 4, the determined position of the tool 3 is forwarded to a position monitoring system 9, or monitoring system for short, that is independent of the robot 2. This system 9 is coupled to an external position-determination system 10, or measurement system in short, which may function optically, such as with video cameras, and detects the position of the tool 3 independently of the robot 2 and of the control system 5 and the position-determination system 7. The position monitoring system 9 compares the measured values, collected or picked up by the control system 5 and the internal position-determination system 7, that indicate the position of the tool 3 and hence of the patient continuously with the measured values furnished by the measurement system 10.

If a deviation that is above an adjustable threshold value is found between the measured values determined by the different position-determination systems 7, 10, then the robot 2, as triggered by the monitoring system 9 via a line 11, is immediately stopped. The intervention by the monitoring system 9 into the motion of the robot 2 is performed close to actuators of the robot 2, so that malfunctions of these actuators can also be detected. In a substantially simple case, the power supply to the robot 2 may be disrupted. However, brakes may be tripped actively.

A first error situation, not shown, which may occur either in the region of the robot 2 with the internal position-determination system 7 or in the region of the external position-determination system 10, may be prevented and safeguarded by a second course, namely the respective other position-determination system 10, 7. The second, external position-determination system 10 may function independently of the robot 2. As such, the position of the tool 3, even if the tool 3 were disconnected from the robot 2, can be correctly detected by the measurement system 10, which is operably configured as an absolute spatial position measurement system.

Moreover, although not shown, the position monitoring system 9 may also be coupled with a collision monitoring system 12 or, together with such a system, forms an integrated safety system. The measurement system 10 can also be utilized to detect impending collisions of components of the examination and/or treatment apparatus 1 with other components of this apparatus 1, or with other objects or persons, in substantially adequate or quick time and optionally to initiate countermeasures automatically, namely stopping the adjusting elements 6 of the robot 2. Data that the control system 5 provides or furnishes, that is, data of the internal position-determination system 7 may also enter into the calculations performed by the collision monitoring system 12. Because the collision monitoring system 12 uses data furnished both by the external position-determination system 10 and by the internal position-determination system 7 relating to the state of motion, that is, the positioning, speed and acceleration, of the tool 3 and further components of the examination and/or treatment apparatus 1, a substantially high degree of reliability of the collision monitoring system 12 may be reached.

Moreover, the examination and/or treatment apparatus 1 is equipped with or includes an acceleration measurement system 13, which uses an acceleration sensor 14 that detects the acceleration of the tool 3 directly. The acceleration measurement system 13, like the collision monitoring system 12, is linked to the monitoring system 9 or may be combined to form an integrated system. If an impermissible acceleration, particularly caused by an impact load, of the tool 3 is detected, then the motion of the tool 3 is stopped. In such a malfunction situation, the tool 3 may be shifted via the robot 2 into a determined secure position, because of the linkage of the acceleration measurement system 13 with the position-determination systems 7, 10 and with the collision monitoring system 12.

The invention claimed is:

1. A medical examination and treatment apparatus, the apparatus comprising:
    a robot operable to move a tool, the robot comprising an adjusting element attached to the tool;
    an internal position-determination system to measure a position of the tool by determining a setting of the adjusting element of the robot, the internal position-determination system being internal to the robot in a same room as the tool and robot;
    an external position-determination system to measure directly the position of the tool while the tool is in a same location when the internal position-determination system measures the position of the tool, the external position-determination system being independent of the robot; and
    a position monitoring system to compare the position of the tool determined by the internal position-determination system with the position of the tool determined by the external position-determination system,
    wherein a mobility of the tool is restricted by restricting the movement of the adjusting element of the robot if an adjustable threshold relating to a deviation between position measurements determined by the comparison is exceeded, and
    wherein the external position-determination system is disposed on the tool and in the room.

2. The medical examination and treatment apparatus of claim 1, wherein the robot is a bent robot arm.

3. The medical examination and treatment apparatus of claim 2, wherein the tool is a patient bed controlled by the robot.

4. The medical examination and treatment apparatus of claim 3, wherein the external position-determination system is an optical measurement system.

5. The medical examination and treatment apparatus of claim 3, wherein the position monitoring system is coupled with a collision monitoring system.

6. The medical examination and treatment apparatus of claim 5, wherein the position monitoring system is coupled with an acceleration measurement system that detects accelerations of the patient bed.

7. The medical examination and treatment apparatus of claim 6, wherein the robot stops the patient bed if an impermissible acceleration of the patient bed is detected by the acceleration measurement system.

8. The medical examination and treatment apparatus of claim 1, wherein the tool is a patient bed controlled by the robot.

9. The medical examination and treatment apparatus of claim 8, wherein the position monitoring system is coupled with an acceleration measurement system that detects accelerations of the patient bed.

10. The medical examination and treatment apparatus of claim 9, wherein the robot stops the patient bed if an impermissible acceleration of the patient bed is detected by the acceleration measurement system.

11. The medical examination and treatment apparatus of claim 1, wherein the external position-determination system is an optical measurement system.

12. The medical examination and treatment apparatus of claim 11, wherein the optical measurement system is a camera-supported system.

13. The medical examination and treatment apparatus of claim 1, wherein the position monitoring system is coupled with a collision monitoring system.

14. The medical examination and treatment apparatus of claim 1, wherein the external position-determination system is configured differently from the internal position-determination system.

15. A method for operating a medical examination and treatment apparatus, the method comprising:
    providing a tool to perform a medical examination or treatment, the tool being moved by a robot connected to a bottom surface of the tool;
    measuring a position of the tool with an internal position-determination system by determining a setting of the robot, the internal position-determination system being internal to the robot in a same room as the patient bed and robot;
    measuring directly the position of the tool with an external position-determination system while the tool is in a same location when the internal position-determination system measures the position of the tool, the external position-determination system being independent of the robot and disposed on the bottom surface of the tool in the room; and
    comparing the position of the tool determined by the internal position-determination system with the position of the tool determined by the external position-determination system,
    wherein a mobility of the tool is restricted by restricting the movement of the adjusting element of the robot if an adjustable threshold relating to a deviation between position measurements determined by the comparison is exceeded.

16. The method of claim 15, wherein the tool is stopped if the deviation between the position measurements is greater than the adjustable threshold.

17. The method of claim 16, wherein the adjustable threshold is dependent on a speed of movement of the tool.

18. The method of claim 15, wherein the adjustable threshold is dependent on a speed of movement of the tool.

19. The method of claim 15 wherein providing comprises providing the robot with adjusting elements, and wherein measuring the position with the internal position-determination system comprises determining a setting of the adjusting elements.

20. The method of claim 19 wherein the comparing is performed continuously and automatically.

21. The method of claim 20, wherein the adjustable threshold is dependent on a speed of movement of the tool.

22. The method of claim 15 wherein the comparing is performed continuously and automatically.

23. The method of claim 22, wherein the tool is stopped if the deviation between the position measurements is greater than the adjustable threshold.

* * * * *